United States Patent [19]

Muntz et al.

[11] 4,014,912
[45] Mar. 29, 1977

[54] METHOD FOR PREPARING ORGANIC VANADATES

[75] Inventors: Ronald L. Muntz, Bedford Hills, N.Y.; Robert W. Lerner, Trumbull, Conn.

[73] Assignee: Stauffer Chemical Company, Adrian, Mich.

[22] Filed: Oct. 16, 1975

[21] Appl. No.: 623,169

[52] U.S. Cl. .......................................... 260/429 R
[51] Int. Cl.$^2$ ........................................ C07F 9/00
[58] Field of Search ............ 260/429 R; 252/431 R

[56] References Cited
UNITED STATES PATENTS

| | | | |
|---|---|---|---|
| 3,652,617 | 3/1972 | Termin et al. | 260/429 |
| 3,657,295 | 4/1972 | McCoy | 260/429 R |
| 3,772,355 | 11/1973 | Merz | 260/429 R |

*Primary Examiner*—Helen M. S. Sneed

[57] ABSTRACT

An improved method for preparing organic vanadates by reacting vanadium oxytrichloride with an alcohol in the presence of ammonia and a hydrocarbon solvent and thereafter adding dimethyl sulfoxide to form two phases, one phase containing the organic vanadates and the other phase being an ammonium chloride-dimethyl sulfoxide suspension.

8 Claims, No Drawings

METHOD FOR PREPARING ORGANIC VANADATES

This invention relates to organic vanadates and more particularly to a method for preparing alkyl and aryl vanadates.

Many methods have been proposed and employed for the preparation of alkyl vanadates. In one method, vanadium pentoxide was reacted with an alcohol to form an alkyl vanadate and water as a by-product, which was then removed as an azeotrope with the excess alcohol. One disadvantage of this method was that it required prolonged heating and caused degradation of the product.

Vanadates, such as butyl vanadate, have been prepared by reacting vanadium oxytrichloride with an excess of butyl alcohol in the presence of ammonia to form butyl vanadate and ammonium chloride. The butyl vanadate solution was separated from the ammonium chloride crystals by filtration. However, since the crystalline ammonium chloride has a tendency to plug the filter, it is difficult to filter off the butyl vanadate. Moreover, the filtration step must be conducted in a closed system to prevent hydrolysis of the butyl vanadate, thus resulting in an expensive process.

It is therefore an object of the present invention to provide a method for preparing organic vanadates. Another object of this invention is to provide a process which eliminates the separation of organic vanadates from ammonium chloride crystals by filtration. A further object of this invention is to provide a process for preparing substantially pure organic vanadates in the absence of distillation.

The foregoing objects and others which will become apparent from the following description are accomplished in accordance with this invention, generally speaking, by reacting an alcohol with vanadium oxytrichloride in the presence of ammonia to form organic vanadates and ammonium chloride. Sufficient dimethyl sulfoxide is added to form two phases, one phase contains the organic vanadates and the other phase contains the dimethyl sulfoxide-ammonium chloride suspension. The organic vanadates are readily separated from the ammonium chloride-dimethyl sulfoxide phase by decantation or any other conventional technique known in the art.

When suitable proportions of reactants are used, the reactions proceed according to the following equations:

wherein each R, which may be the same or different, represents a monovalent hydrocarbon radical having from 2 to 10 carbon atoms. More specifically each R can be, for example, an alkyl radical such as ethyl, propyl, butyl, hexyl, 2-ethylhexyl, or octyl, or an aryl radical such as phenyl or a hydrocarbon substituted phenyl radical.

Generally, when vanadium oxytrichloride is admixed with the alcohol an exothermic reaction takes place which releases a quantity of hydrogen chloride. It is desirable to remove as much of the liberated hydrogen chloride from the mixture as possible before adding ammonia in order to reduce the formation of ammonium chloride by-product. This may be accomplished by passing a stream of an inert gas, e.g., krypton, xenon, radon, argon, helium, nitrogen, or carbon dioxide through the reaction mixture to sweep out a portion of the hydrogen chloride released prior to the addition of ammonia. Upon completion of the reaction, dimethyl sulfoxide is added to the reaction mixture, thereby resulting in the formation of two liquid phases, one being the organic vanadate and the other being the dimethyl sulfoxide-ammonium chloride suspension. The vanadate product may be separated by decantation or any other conventional technique known in the art.

Although it is not essential, it is preferred that the reaction between vanadium oxytrichloride and an alcohol be conducted in the presence of a hydrocarbon solvent. Any hydrocarbon solvent which is a solvent for the organic vanadate and which is a nonsolvent for the ammonium chloride and is immiscible with dimethyl sulfoxide may be used in the process of this invention. Preferably the hydrocarbon solvent is an inert aliphatic hydrocarbon, such as pentane, hexane, octane, decane, dodecane, and the like. A mixture of solvents may be used, if desired.

Although the amount of hydrocarbon solvent present during the reaction is not critical, a sufficient amount should be present to form a polar layer and a non-polar layer. Generally, the amount of hydrocarbon solvent should be in a weight ratio of solvent to vanadium oxytrichloride of from about 1:1 to about 5:1 and more preferably from about 2:1 to 4:1. The upper limit is primarily dependent on economic considerations.

The vanadium oxytrichloride and alcohol are preferably employed in a molar ratio of about 1:3; however, they may be employed in a molar ratio of from 1:1 to 1:5. Where the molar ratio is less than 1:3, the resulting product will consist of vanadium oxychloride having organic groups substituted thereon.

The reactants are maintained together at a temperature and for a time sufficient to produce the desired vanadate product. The latitude of the temperature is such that the reaction can be conducted from about 0° up to about 100° C. and more preferably from about 20° C. to about 70° C. The time for the reaction is from several minutes to several hours, e.g., from about 1 to about 8 hours. In most cases, the reaction will be completed in from 2 to 6 hours. When the reaction is adjusted to operate at optimum conditions, maximum yields of organic vanadates are obtained with minimal degradation.

Although the reaction is normally run at atmospheric pressure, it can be run at sub-atmospheric or super-atmospheric pressures in either a batch, semi-continuous, or continuous process.

The dimethyl sulfoxide may be added to the reaction mixture prior to or during the reaction or prior to or subsequent to the addition of ammonia. Preferably, however, the dimethyl sulfoxide is added after the ammonia addition has been completed.

The amount of dimethyl sulfoxide present is not critical and may vary over a range of from 1 to 10 times the weight of the vanadium oxytrichloride. When the dimethyl sulfoxide is present in a weight ratio of about 1:1 with the vanadium oxytrichloride, the ammonium chloride is difficult to separate from the organic vanadate. Preferably the weight ratio of dimethyl sulfoxide to vanadium oxytrichloride is from 1.5:1 to 10:1 and more preferably from about 2:1 to about 5:1.

If desired, the organic vanadates may be further purified by distillation or other conventional means. If the organic vanadate is to be distilled or if for any reason it is desired to heat the organic vanadate, it is preferred that it be heated under anhydrous conditions.

Moreover, the initial reactants should be substantially free of water, since the presence of moisture causes hydrolysis of the vanadate and thus results in lower yields. Ideally, a inert gas should blanket the system to prevent decomposition of the product.

The organic vanadate products of the present invention may be used in combination with aluminum alkyls as catalysts for polymerizing olefins to make elastomeric material.

Various embodiments of this invention are further illustrated by the following examples in which all parts are by weight unless otherwise specified.

EXAMPLE 1

To a reactor containing about 166 parts of n-butyl alcohol are added about 86 parts of vanadium oxytrichloride with agitation and external cooling while sparging with nitrogen. After about two hours, ammonia is bubbled through the reaction mixture for about two hours and then about 172 parts of dimethyl sulfoxide is added to reaction product with agitation while maintaining the temperature below about 30° C. The contents of the reactor are transferred to a separatory funnel where they separate into two layers, an upper layer and a lower layer of dimethyl sulfoxide-ammonium chloride by-product. The upper layer is separated from the lower layer by decantation and analyzed. A product is obtained which is identified as tri-n-butyl vanadate.

EXAMPLE 2

In accordance with the procedure described in Example 1, about 208 parts of 2-ethylhexyl alcohol is substituted for n-butyl alcohol. Two layers are formed, one layer being the dimethyl sulfoxide-ammonium chloride by-product and the other containing a product which is identified as tri-2-ethylhexyl vanadate.

EXAMPLE 3

About 141 parts of vanadium oxytrichloride and about 165 parts of hexane are added to a reactor equipped with an agitator and external cooling while sparging with nitrogen. About 79 parts of a mixture containing 85 parts of hexane and 123 parts of ethanol are added to the reactor with agitation and slow nitrogen sparging over a one hour period followed by refluxing for an additional hour. The mixture is cooled to about 50° C. and ammonia is bubbled into the reaction mixture while the remainder of the ethanol-hexane mixture is added dropwise. After two hours, the ethanol addition is complete while a positive pressure of ammonia is maintained in the reactor for an additional hour, then about 335 parts of dimethyl sulfoxide are added with agitation. The contents of the reactor are transferred to a separatory funnel where they separate into two phases, an upper phase and a lower phase which is the dimethyl sulfoxide-ammonium chloride suspension.

The upper phase is separated from the lower phase by decantation and the solvent is distilled off under vacuum. A product is recovered which is identified as tri-ethyl vanadate.

EXAMPLE 4

About 141 parts of vanadium oxytrichloride and about 165 parts of hexane are added to a reactor equipped with an agitator and eternal cooling means while sparging with nitrogen. About 208 parts of a mixture containing 85 parts of hexane and 123 parts of ethanol are added to the reactor dropwise with agitation and slow nitrogen sparging over a period of about 2 hours. The mixture is cooled to about 50° C and about 335 parts of dimethyl sulfoxide is added to the reaction mixture. Ammonia is bubbled into the reaction mixture for about 2 hours and then the contents of the reactor are transferred to a separatory funnel where they separate into two layers, an upper layer containing the tri-ethyl vanadate and a lower layer containing the dimethyl sulfoxide-ammonium chloride suspension.

EXAMPLE 5

The procedure of Example 4 is repeated except that toluene is substituted for hexane as the solvent. Again two phases are formed with the tri-ethyl vanadate in the upper phase and the dimethyl sulfoxide-ammonium chloride in the lower phase.

Although the present invention has been defined specifically with reference to the above given examples, it should be understood that these examples were given only for purposes of illustration. Other variations which will become apparent to those skilled in the art are intended to be included within the scope of this invention.

The invention claimed is:

1. A process for preparing organic vanadates which comprises reacting vanadium oxytrichloride with a monohydric alcohol having from 2 to 10 carbon atoms in a molar ratio of vanadium oxytrichloride to alcohol of from 1:1 to 1:5 in the presence of ammonia at a temperature of from about 0° up to about 100° C under substantially anhydrous conditions and thereafter adding sufficient dimethyl sulfoxide to the reaction mixture to form a vanadate phase and a dimethyl sulfoxide-ammonium chloride phase and thereafter recovering the organic vanadate.

2. The process of claim 1 wherein an inert gas is passed through the reaction mixture to remove hydrogen chloride prior to the addition of ammonia.

3. The process of claim 1 wherein the vanadium oxytrichloride and alcohol are reacted in the presence of ammonia and a hydrocarbon solvent.

4. The process of claim 3 wherein the reaction mixture also contains dimethyl sulfoxide.

5. The process of claim 1 wherein the monohydric alcohol contains an alkyl radical having from 2 to 10 carbon atoms.

6. The process of claim 1 wherein the alcohol is n-butyl alcohol.

7. The process of claim 1 wherein the vanadium oxytrichloride and the monohydric alcohol are reacted at a temperature below 70° C.

8. The process of claim 1 wherein the alcohol is ethyl alcohol.

* * * * *